US011676056B2

(12) United States Patent
Ollitrault et al.

(10) Patent No.: US 11,676,056 B2
(45) Date of Patent: Jun. 13, 2023

(54) CALCULATING EXCITED STATE PROPERTIES OF A MOLECULAR SYSTEM USING A HYBRID CLASSICAL-QUANTUM COMPUTING SYSTEM

(71) Applicant: International Business Machines Corporation, Armonk, NY (US)

(72) Inventors: Pauline Ollitrault, Zurich (CH); Panagiotis Barkoutsos, Zurich (CH); Stefan Woerner, Zurich (CH); Marco Pistoia, Amawalk, NY (US); Antonio Mezzacapo, Westchester, NY (US); Ivano Tavernelli, Zurich (CH)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 1022 days.

(21) Appl. No.: 16/369,885

(22) Filed: Mar. 29, 2019

(65) Prior Publication Data
US 2020/0311589 A1 Oct. 1, 2020

Related U.S. Application Data

(60) Provisional application No. 62/729,686, filed on Sep. 11, 2018.

(51) Int. Cl.
*G06N 10/00* (2022.01)
*G06F 15/16* (2006.01)
(Continued)

(52) U.S. Cl.
CPC ............. *G06N 10/00* (2019.01); *G06F 15/16* (2013.01); *G06F 17/14* (2013.01); *G06F 17/16* (2013.01)

(58) Field of Classification Search
CPC .......... G06F 15/16; G06F 17/14; G06F 17/16; G06N 10/00; G06N 5/003; G16C 10/00; G16C 20/90
See application file for complete search history.

(56) References Cited

U.S. PATENT DOCUMENTS 7,276,103 B2   10/2007   Woste et al.
7,554,080 B2   6/2009    Munro et al.
(Continued)

FOREIGN PATENT DOCUMENTS

JP    202014440 A      1/2020
WO   2015123083 A2    8/2015
WO   2018033823 A1    2/2018

OTHER PUBLICATIONS

Barkoutsos et al. "Quantum algorithms for electronic structure calculations: particle/hole Hamiltonian and optimized wavefunction expansions", arxiv.org, Cornell University Library, 201 Olin Library, Cornell University, Ithaca, NY 14853, published May 14, 2018 (Year: 2018).*

(Continued)

*Primary Examiner* — Terrell S Johnson
(74) *Attorney, Agent, or Firm* — Garg Law Firm, PLLC; Rakesh Garg; Erik Johnson

(57) ABSTRACT

A method for calculating excited state properties of a molecular system using a hybrid classical-quantum computing system includes determining, using a quantum processor and memory, a ground state wavefunction of a combination of quantum logic gates. In an embodiment, the method includes forming a set of excitation operators. In an embodiment, the method includes forming a set of commutators from the set of excitation operators and a Hamiltonian operator. In an embodiment, the method includes mapping the set of commutators onto a set of qubit states, the set of qubit states corresponding to a set of qubits of the quantum (Continued)

processor. In an embodiment, the method includes evaluating, using the quantum processor and memory, the set of commutators. In an embodiment, the method includes causing a quantum readout circuit to measure an excited state energy from the set of computed commutators.

20 Claims, 8 Drawing Sheets

(51) Int. Cl.
*G06F 17/14* (2006.01)
*G06F 17/16* (2006.01)

(56) References Cited

U.S. PATENT DOCUMENTS

| | | |
|---|---|---|
| 2009/0182542 A9 | 12/2001 | Hilton et al. |
| 2005/0023127 A1 | 2/2005 | Woste et al. |
| 2005/0273306 A1 | 12/2005 | Hilton et al. |
| 2007/0252081 A1 | 11/2007 | Munro et al. |
| 2010/0318331 A1 | 12/2010 | Ritchie |
| 2017/0228483 A1 | 8/2017 | Rigetti et al. |

OTHER PUBLICATIONS

International Searching Authority, PCT/EP2019/073651, P201806864PCT01, dated Dec. 9, 2019.
Response Communication pursuant to Rules 162(1) and 162 EPC, Application No. 19765238.1-1203, dated Oct. 18, 2021.
Zhao et al., "Equation of motion theory for excited states in variational Monte Carlo and the Jastrow antisymmetric geminal power in Hilbert space", 2016. https://arxiv.org/pdf/1605.03527.pdf.
Ganzhorn et al., Gate-efficient simulation of molecular eigenstates on a quantum computer, Aug. 24, 2018.
Colless et al., Robust determination of molecular spectra on a quantum processor, Jul. 20, 2017.
A quantum computing algorithm for the investigation of the molecular excited states. Sep. 3, 2018.
Higgott et al., Variational Quantum Computation of Excited States, May 21, 2018.
McClean et al., Hybrid Quantum-Classical Hierarchy for Mitigation of Decoherence and Determination of Excited States, Mar. 17, 2016.
Application No. 2021-512897, Receive Notice of Allowance, dated Jan. 30, 2023.
Application No. 2021-512897, Receive Notice of Allowance English Translation, dated Jan. 30, 2023.

* cited by examiner

CALCULATING EXCITED STATE PROPERTIES OF A MOLECULAR SYSTEM USING A HYBRID CLASSICAL-QUANTUM COMPUTING SYSTEM

TECHNICAL FIELD

The present invention relates generally to optimization using quantum computing. More particularly, the present invention relates to a system and method for calculating excited state properties of a molecular system using a hybrid classical-quantum computing system.

BACKGROUND

Hereinafter, a "Q" prefix in a word of phrase is indicative of a reference of that word or phrase in a quantum computing context unless expressly distinguished where used.

Molecules and subatomic particles follow the laws of quantum mechanics, a branch of physics that explores how the physical world works at the most fundamental levels. At this level, particles behave in strange ways, taking on more than one state at the same time, and interacting with other particles that are very far away. Quantum computing harnesses these quantum phenomena to process information.

The computers we commonly use today are known as classical computers (also referred to herein as "conventional" computers or conventional nodes, or "CN"). A conventional computer uses a conventional processor fabricated using semiconductor materials and technology, a semiconductor memory, and a magnetic or solid-state storage device, in what is known as a Von Neumann architecture. Particularly, the processors in conventional computers are binary processors, i.e., operating on binary data represented by 1 and 0.

A quantum processor (q-processor) uses the unique nature of entangled qubit devices (compactly referred to herein as "qubit," plural "qubits") to perform computational tasks. In the particular realms where quantum mechanics operates, particles of matter can exist in multiple states—such as an "on" state, an "off" state, and both "on" and "off" states simultaneously. Where binary computing using semiconductor processors is limited to using just the on and off states (equivalent to 1 and 0 in binary code), a quantum processor harnesses these quantum states of matter to output signals that are usable in data computing.

Conventional computers encode information in bits. Each bit can take the value of 1 or 0. These 1s and 0s act as on/off switches that ultimately drive computer functions. Quantum computers, on the other hand, are based on qubits, which operate according to two key principles of quantum physics: superposition and entanglement. Superposition means that each qubit can represent both a 1 and a 0 inference between possible outcomes for an event. Entanglement means that qubits in a superposition can be correlated with each other in a non-classical way; that is, the state of one (whether it is a 1 or a 0 or both) can depend on the state of another, and that there is more information contained within the two qubits when they are entangled than as two individual qubits.

Using these two principles, qubits operate as processors of information, enabling quantum computers to function in ways that allow them to solve certain difficult problems that are intractable using conventional computers.

A class of problems exists called optimization problems. An optimization problem is a computational problem in which the best or optimal solution is to be determined for a different problem where the different problem has several possible solutions. For example, the different problem can be the famous traveling salesman problem where a route has to be determined between several cities such that a traveling salesman covers each of the of cities without revising any of the cities. This problem has many possible solutions—routes between the cities. An optimization problem related to the traveling salesman problem is to find the shortest—i.e., the best or most optimal route—from the many possible routes, each of which satisfies the requirements of the traveling salesman problem.

Configuring an optimization problem for execution on a computer so that the computer can compute the optimal solution in finite time is a difficult problem in itself. Until recently, the only computing resources available for executing optimization problems were the conventional computers as described herein. Many optimization problems are too difficult or too complex for conventional computers to compute in finite time with reasonable resources. Generally, an approximated solution which can be computed in reasonable time and with reasonable resources is accepted as the near-optimal solution in such cases.

The advent of quantum computing has presented advancement possibilities in many areas of computing, including the computation of optimization problems. Because a quantum computing system can evaluate many solutions from the solution space at once, the illustrative embodiments recognize that such systems are particularly suitable for solving optimization problems.

The illustrative embodiments recognize that several quantum computing methods have been proposed for solving the electronic structure of molecular systems. The electronic structure of molecular systems are governed by the interactions among electronic orbitals in the molecules. The state of a molecular system is the arrangement of molecular orbitals which describe the wave-like behavior of an electron in a molecule. The ground state corresponds to the lowest energy state of the molecular system. Excited energy states correspond to discrete energy differences greater than the ground state.

The illustrative embodiments recognize that quantum processors can perform variational algorithms which presently available conventional processors are either incapable of performing or can only perform with undesirable accuracy or computational resource consumption. Variational algorithms use a trial wavefunction which is varied to determine an upper bound to a ground state energy of a quantum system. A wavefunction is a mathematical description, such as, of a quantum state of a quantum system. A quantum state is represented on a quantum processor as a series of quantum logic gates acting on qubits. Each quantum state of a quantum system includes a corresponding energy value.

The energy of the ground state of the quantum system corresponds to a minimum possible value of the ground state energy of the quantum system. A Hamiltonian is a matrix operator that describes the ground state energy of a quantum state. A Hamiltonian operator acting on a wavefunction determines a value corresponding to the ground state energy of the quantum state.

In order to compute an upper bound to the ground state energy of a quantum system, variational algorithms perform numerous evaluations beginning with an initial wavefunction. Each evaluation computes a ground state energy of a quantum state corresponding to the wavefunction being evaluated. Variational algorithms can then alter parameters of the evaluated wavefunction to generate a new wavefunction, such as, altering at least one quantum logic gate of a set of quantum logic gates to perform a rotation on a qubit. Evaluation of the new wavefunction computes a ground state energy of the new quantum state corresponding to the new wavefunction. The variational algorithm compares the ground state energy of the previous wavefunction to the ground state energy of the new wavefunction.

A conventional processor executes an optimization algorithm that varies the parameters of the wavefunction. A quantum processor computes the corresponding ground state energy of the wavefunction. Based on the comparison between the ground state energy of the new wavefunction and the previous wavefunction, the optimization algorithm determines how to vary the parameters of the wavefunction in order to minimize the computed ground state energy of the quantum system.

A variational algorithm can continue performing evaluations until the computed ground state energy is relatively stable, such as, successive evaluations computing a ground state energy within a threshold percentage. The stable computed ground state energy from the final evaluation corresponds to an upper bound of the minimum energy of the ground state of the quantum system. The corresponding wavefunction represents an approximation of the eigenfunction of the quantum system.

The illustrative embodiments recognize that presently available methods are inaccurate for determining excited state energies of a quantum system. Quantum subspace expansion (QSE) is a method for computing excited state energies of a quantum system. The illustrative embodiments recognize that QSE is based on perturbation theory. Perturbation theory involves beginning with a simple system with a known mathematical solution before adding additional elements to approximate a more complex system. The illustrative embodiments recognize that QSE exhibits certain drawbacks. The illustrative embodiments recognize that QSE is unavailable for certain quantum systems without a similar simple system. The illustrative embodiments further recognize that QSE is prohibitively computationally expensive in the number of measurements required.

Witness-Assisted Variational Eigenspectra Solver (WAVES) is another method for determining excited state energies of a quantum system. WAVES involves a variational search for the ground state of a quantum system, a second variational search for excited states, and an Iterative Phase Estimation Algorithm (IPEA) to approximate the excited state energies. The illustrative embodiments recognize that WAVES exhibits certain drawbacks. The illustrative embodiments recognize that WAVES requires a time consuming variational optimization of each excited state.

SUMMARY

The illustrative embodiments provide a method, system, and computer program product for calculating excited state properties of a molecular system using a hybrid classical-quantum computing system. An embodiment of a method includes determining, using a quantum processor and memory, a ground state wavefunction of a combination of quantum logic gates, the quantum processor comprising a set of quantum logic gates configured to perform single qubit rotations.

In an embodiment, the method includes forming a set of excitation operators, the set of excitation operators configured to determine an excited state wavefunction from the ground state wavefunction. In an embodiment, the method includes forming a set of commutators from the set of excitation operators and a Hamiltonian operator, the Hamiltonian operator configured to determine a ground state energy of a wavefunction.

In an embodiment, the method includes mapping the set of commutators onto a set of qubit states, the set of qubit states corresponding to a set of qubits of the quantum processor. In an embodiment, the method includes evaluating, using the quantum processor and memory, the set of commutators. In an embodiment, the method includes causing a quantum readout circuit to measure an excited state energy from the set of computed commutators.

In an embodiment, the method includes extracting a set of Pauli strings, each Pauli string of the set of Pauli strings comprising a set of Pauli operators. In an embodiment, the method includes evaluating the set of Pauli strings to compute the set of commutators.

In an embodiment, the method includes grouping a subset of the set of Pauli strings, the subset corresponding to at least one of the set of commutators. In an embodiment, the method includes mapping the set of excitation operators using Jordan-Wigner transformation.

In an embodiment, the set of commutators are mapped using Jordan-Wigner transformation. In an embodiment, the method includes computing a set of matrix elements for a secular matrix equation corresponding to an eigenvalue equation for a set of excitation energies.

An embodiment includes a computer usable program product. The computer usable program product includes a computer-readable storage device, and program instructions stored on the storage device.

An embodiment includes a computer system. The computer system includes a processor, a computer-readable memory, and a computer-readable storage device, and program instructions stored on the storage device for execution by the processor via the memory.

BRIEF DESCRIPTION OF THE DRAWINGS

The novel features believed characteristic of the invention are set forth in the appended claims. The invention itself, however, as well as a preferred mode of use, further objectives and advantages thereof, will best be understood by reference to the following detailed description of the illustrative embodiments when read in conjunction with the accompanying drawings, wherein:

DETAILED DESCRIPTION

Figure 1:
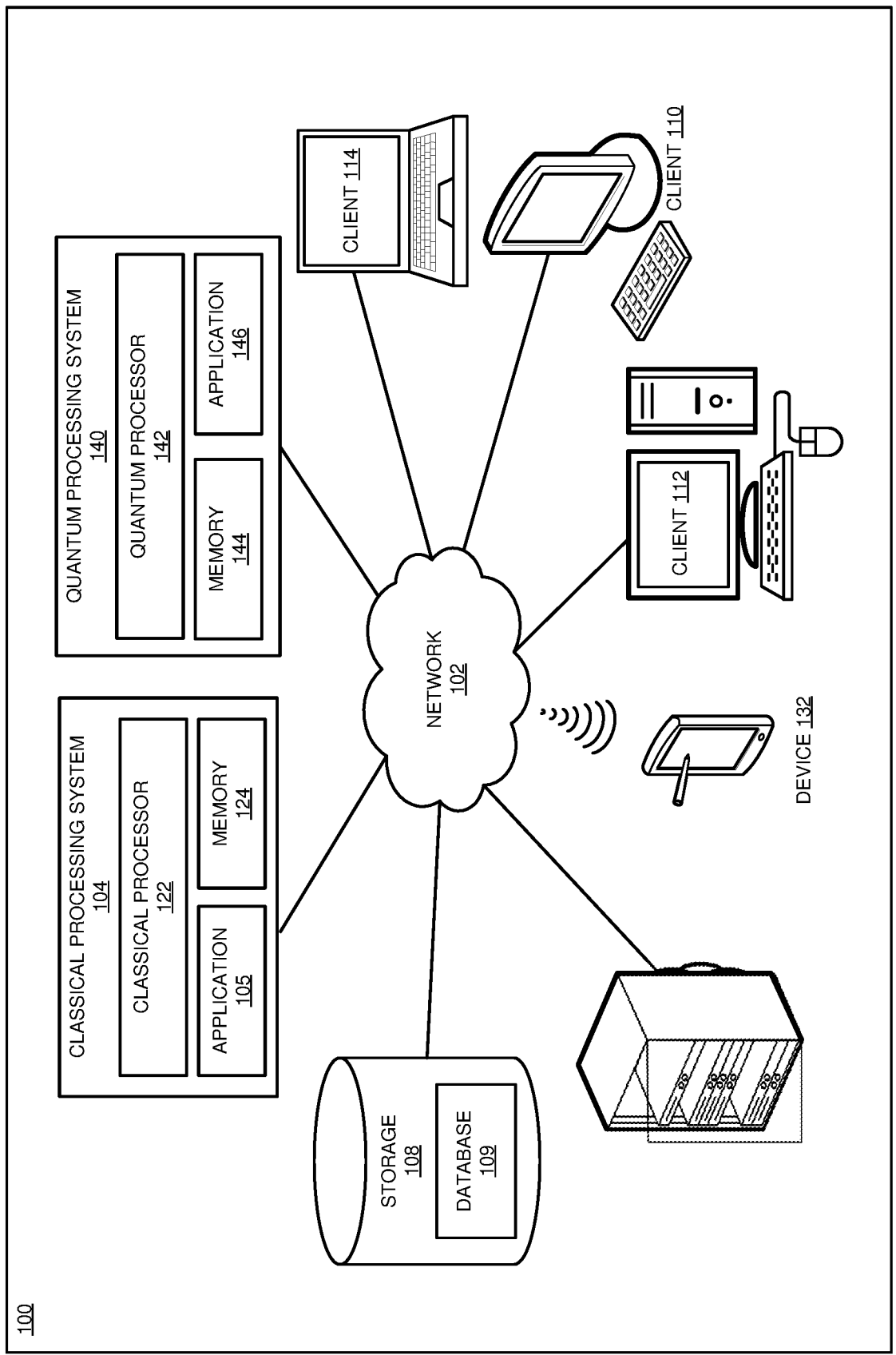
FIG. 1 depicts a block diagram of a network of data processing systems in which illustrative embodiments may be implemented.

The illustrative embodiments used to describe the invention generally address and solve the above-described problem of solving computational problems using quantum computing. The illustrative embodiments provide a method and system for calculating excited state properties of a molecular system using a hybrid classical-quantum computing system.

Solution optimization is a well-recognized technological field of endeavor. Quantum computing using processors formed from quantum qubits is another well recognized technological field of endeavor. The present state of the technology in a combination of these two fields of endeavor has certain drawbacks and limitations. The operations and/or configurations of the illustrative embodiments impart additional or new capabilities to improve the existing technology in these technological fields of endeavor, especially in configuring optimization problems for execution in quantum computing environments.

The illustrative embodiments recognize that solving an optimization problem in quantum computing typically requires translating the optimization problem, along with its inputs, into a Hamiltonian, and then passing the Hamiltonian to a quantum variational algorithm, such as the Variational Quantum Eigensolver (VQE) algorithm and the Quantum Approximate Optimization Algorithm (QAOA).

An embodiment provides a method for calculating excited state properties of a molecular system using hybrid classical-quantum computing system. Another embodiment provides a conventional or quantum computer usable program product comprising a computer-readable storage device, and program instructions stored on the storage device, the stored program instructions comprising a method for calculating excited state properties of a molecular system using hybrid classical-quantum computing system. The instructions are executable using a conventional or quantum processor. Another embodiment provides a computer system comprising a conventional or quantum processor, a computer-readable memory, and a computer-readable storage device, and program instructions stored on the storage device for execution by the processor via the memory, the stored program instructions comprising a method for calculating excited state properties of a molecular system using hybrid classical-quantum computing system.

The illustrative embodiments recognize that quantum processors can perform variational algorithms to compute an approximation of the ground state energy of a quantum system, for instance, an electron orbital configuration for a molecule with a given interatomic spacing. The Variational Quantum Eigensolver (VQE) is one example of a variational algorithm performed with quantum processors. VQE varies parameters to prepare a quantum state and determines the properties of prepared quantum states. A quantum state is prepared on a quantum processor as a series of quantum logic gates acting on qubits.

The illustrative embodiments recognize that the initial quantum state (wavefunction) may be randomly chosen because the eigenfunction of the quantum system is either unknown or too complex. The variational algorithm performs evaluations of the quantum states to determine properties, such as a ground state energy, of the initial quantum state, vary parameters, such as varying rotational angles of a set of single qubit quantum logic rotation gates, to prepare a new quantum state, determine properties of the new quantum state, and compare the properties of the initial quantum state and the new quantum state.

Variational algorithms iterate to generate new quantum states and to minimize a property corresponding to the quantum states. Variational algorithms include an optimizer to minimize a property corresponding to the quantum states. Each evaluation performed by the variational algorithm includes varying parameters, such as single qubit rotations, to generate a new quantum state, computing properties of the new quantum state, comparing properties of the new quantum state and a previous quantum state, and determining, based on the comparison, how to vary the parameters in a successive evaluation to compute a ground state energy of the quantum system. For instance, the variational algorithm can perform evaluations to determine an upper bound of the ground state energy of the quantum system.

The variational algorithm varies one or more parameters to generate one or more new quantum states and compares the ground state energy of a new quantum state to a ground state energy of one or more previous quantum states. The optimizer determines which parameter(s) and/or how to vary the parameter(s) to reduce the computed ground state energy of the generated quantum state(s). The variational algorithm continues performing evaluations until the computed ground state energy reaches a minimum, becoming relatively stable. The computed ground state energy for the final evaluation corresponds to an upper bound of the ground state energy of the quantum system.

Excited states $|n\rangle$ can be created by applying an excitation matrix operator $O_n^\dagger$ on the ground state $|0\rangle$ of the quantum system. The excitation matrix operator is defined as, $O_n^\dagger = |n\rangle\langle 0|$. Similarly, a de-excitation operator is defined as, $O_n = |0\rangle\langle n|$. A commutator of the excitation operator and the Hamiltonian operator is defined as, $[\hat{H}, O_n^\dagger] = \hat{H} O_n^\dagger - O_n^\dagger \hat{H}$. Taking the commutator of the Hamiltonian and the excitation operator leads to an expression for the excitation energies, $\Delta E_{0n} = E_n - E_0$, of the system as $[\hat{H}, O_n^\dagger]|0\rangle = \hat{H} O_n^\dagger |0\rangle - O_n^\dagger \hat{H}|0\rangle = (E_n - E_0) O_n^\dagger |0\rangle$.

A useful form of the excitation energy, $\Delta E_{0n}$, is obtained by operating with the excitation operator on the previous equation from the left side, $$\Delta E_{0n} = \frac{\langle 0|[O_n, \hat{H}, O_n^\dagger]|0\rangle}{\langle 0|[O_n, O_n^\dagger]|0\rangle}.$$

The excitation operator can be expressed as a linear expansion of basis operators and optimizing the expansion coefficients. The simplest basis is composed of Fermionic creation and annihilation operators, $\alpha^\dagger$, $\alpha$ in which $\alpha_m^\dagger$, $\alpha_i$ represents the excitation of a single electron from an occupied orbital i to a virtual orbital m. The Fermionic operators can be mapped to Pauli operators by a Jordan-Wigner transformation defined by:

$$\alpha_j^\dagger = 1^{\otimes i-1} \otimes \sigma_i^z \otimes (\sigma_j^x - i\sigma_j^y)(\sigma^z)^{\otimes N-i}$$

$$\alpha_j = 1^{\otimes i-1} \otimes \sigma_i^z \otimes (\sigma_j^x + i\sigma_j^y)(\sigma^z)^{\otimes N-i}$$

where N is the total number of qubits.

The excitation operator can then be expressed as $O_n^\dagger = \Sigma_\alpha \Sigma_{\mu_\alpha} [X_{\mu_\alpha}^{(\alpha)} E_{\mu_\alpha}^{(\alpha)} - Y_{\mu_\alpha}^{(\alpha)} (E_{\mu_\alpha}^{(\alpha)})^\dagger]$, where $\alpha$ is the degree of excitation and $E_{\mu_1}^{(1)} = a_m^\dagger a_i$, $E_{\mu_2}^{(2)} = a_m^\dagger a_n^\dagger a_i a_j$. The variation with respect to the $X_{\mu_\alpha}^{(\alpha)}$ and $Y_{\mu_\alpha}^{(\alpha)}$ parameters, $\delta(E_{0n}) = 0$, leads to the secular matrix equation for determining eigenvalues (excitation energies) of the molecular system, $$\begin{pmatrix} M & Q \\ Q^* & M^* \end{pmatrix} \begin{pmatrix} X_n \\ Y_n \end{pmatrix} = \omega_n \begin{pmatrix} V & W \\ -W^* & -V^* \end{pmatrix} \begin{pmatrix} X_n \\ Y_n \end{pmatrix}$$

where:

$$M_{\mu_\alpha \nu_\beta} = \langle 0|[(E_{\mu_\alpha}^{(\alpha)})^\dagger, \hat{H}, E_{\nu_\beta}^{(\beta)}]|0\rangle$$

$$Q_{\mu_\alpha \nu_\beta} = -\langle 0|[(E_{\mu_\alpha}^{(\alpha)})^\dagger, \hat{H}, (E_{\nu_\beta}^{(\beta)})^\dagger]|0\rangle$$

$$V_{\mu_\alpha \nu_\beta} = \langle 0|[(E_{\mu_\alpha}^{(\alpha)})^\dagger, E_{\nu_\beta}^{(\beta)}]|0\rangle$$

$$W_{\mu_\alpha \nu_\beta} = -\langle 0|[(E_{\mu_\alpha}^{(\alpha)})^\dagger, (E_{\nu_\beta}^{(\beta)})^\dagger]|0\rangle$$

and $\omega_n$ is the excitation energy.

One or more embodiments provide for a mixed classical and quantum methodology that calculates excited state properties of molecular systems. In one or more embodiments, a classical computer is used to optimize parameters and evaluate the matrix equations, and a quantum computer is used to compute the matrix elements.

In an embodiment, the commutators of the Hamiltonian operator and the excitation operators are mapped onto a set of qubit states. In particular embodiments, the commutators are mapped from Fermionic operators to Pauli operators using Jordan-Wigner transformation. In the embodiment, the ground state wavefunction is determined. In the embodiment the ground state wavefunction is parameterized in a set of angles.

For the clarity of the description, and without implying any limitation thereto, the illustrative embodiments are described using some example configurations. From this disclosure, those of ordinary skill in the art will be able to conceive many alterations, adaptations, and modifications of a described configuration for achieving a described purpose, and the same are contemplated within the scope of the illustrative embodiments.

Furthermore, simplified diagrams of the data processing environments are used in the figures and the illustrative embodiments. In an actual computing environment, additional structures or component that are not shown or described herein, or structures or components different from those shown but for a similar function as described herein may be present without departing the scope of the illustrative embodiments.

Furthermore, the illustrative embodiments are described with respect to specific actual or hypothetical components only as examples. The steps described by the various illustrative embodiments can be adapted for calculating excited state energies of a molecular system using a variety of components that can be purposed or repurposed to provide a described function within a data processing environment, and such adaptations are contemplated within the scope of the illustrative embodiments.

The illustrative embodiments are described with respect to certain types of steps, applications, classical processors, quantum processors, quantum states, classical feature spaces, quantum feature spaces, and data processing environments only as examples. Any specific manifestations of these and other similar artifacts are not intended to be limiting to the invention. Any suitable manifestation of these and other similar artifacts can be selected within the scope of the illustrative embodiments.

The examples in this disclosure are used only for the clarity of the description and are not limiting to the illustrative embodiments. Any advantages listed herein are only examples and are not intended to be limiting to the illustrative embodiments. Additional or different advantages may be realized by specific illustrative embodiments. Furthermore, a particular illustrative embodiment may have some, all, or none of the advantages listed above.

Figure 2:
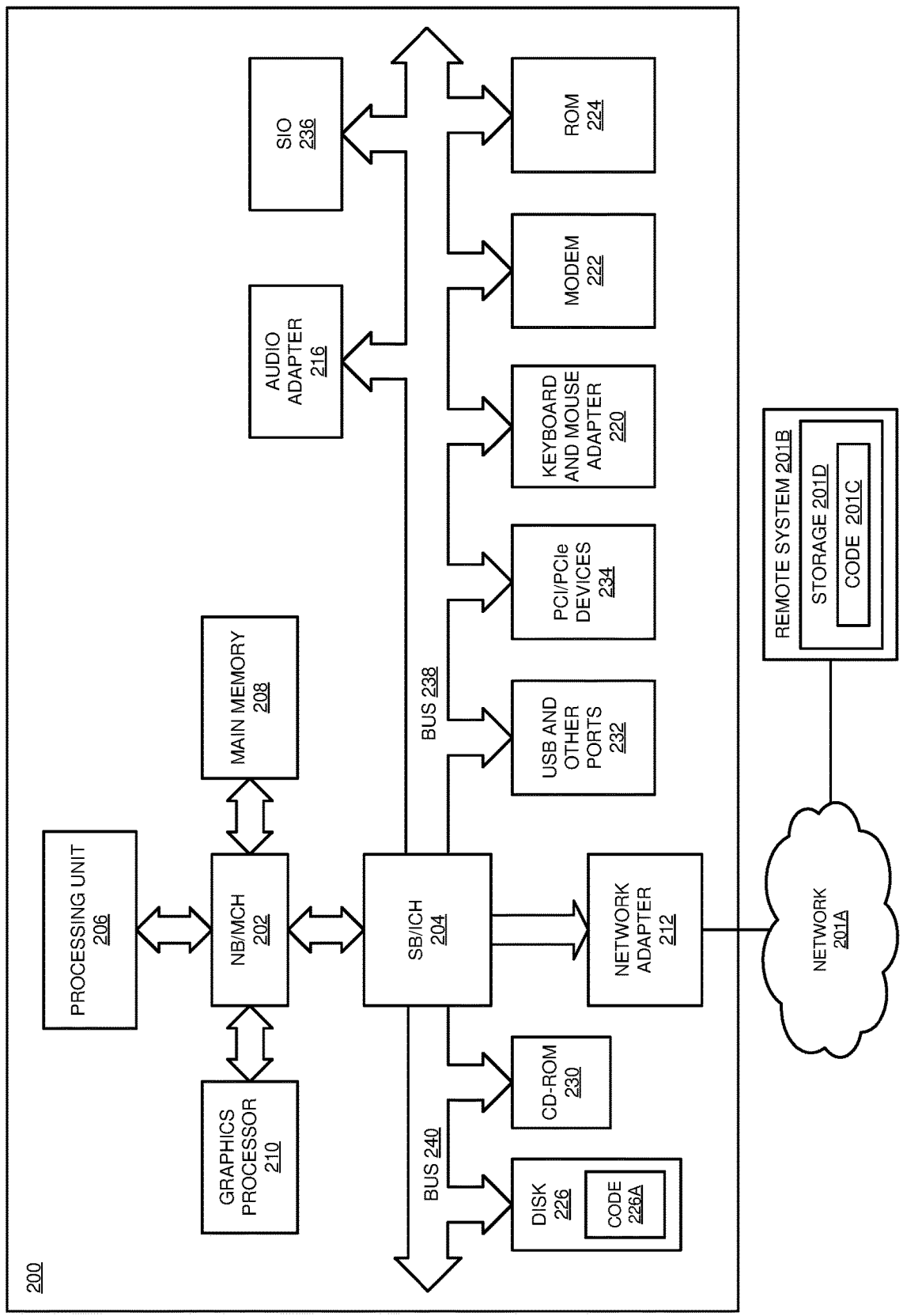
FIG. 2 depicts a block diagram of a data processing system in which illustrative embodiments may be implemented.

With reference to the figures and in particular with reference to FIGS. 1 and 2, these figures are example diagrams of data processing environments in which illustrative embodiments may be implemented. FIGS. 1 and 2 are only examples and are not intended to assert or imply any limitation with regard to the environments in which different embodiments may be implemented. A particular implementation may make many modifications to the depicted environments based on the following description.

FIG. 1 depicts a block diagram of a network of data processing systems in which illustrative embodiments may be implemented. Data processing environment 100 is a network of computers in which the illustrative embodiments may be implemented. Data processing environment 100 includes network 102. Network 102 is the medium used to provide communications links between various devices and computers connected together within data processing environment 100. Network 102 may include connections, such as wire, wireless communication links, or fiber optic cables.

Clients or servers are only example roles of certain data processing systems connected to network 102 and are not intended to exclude other configurations or roles for these data processing systems. Classical processing system 104 couples to network 102. Classical processing system 104 is a classical processing system. Software applications may execute on any quantum data processing system in data processing environment 100. Any software application described as executing in classical processing system 104 in FIG. 1 can be configured to execute in another data processing system in a similar manner. Any data or information stored or produced in classical processing system 104 in FIG. 1 can be configured to be stored or produced in another data processing system in a similar manner. A classical data processing system, such as classical processing system 104, may contain data and may have software applications or software tools executing classical computing processes thereon.

Server 106 couples to network 102 along with storage unit 108. Storage unit 108 includes a database 109 configured to store parameters for a quantum state. Server 106 is a conventional data processing system. Quantum processing system 140 couples to network 102. Quantum processing system 140 is a quantum data processing system. Software applications may execute on any quantum data processing system in data processing environment 100. Any software application described as executing in quantum processing system 140 in FIG. 1 can be configured to execute in another quantum data processing system in a similar manner. Any data or information stored or produced in quantum processing system 140 in FIG. 1 can be configured to be stored or produced in another quantum data processing system in a similar manner. A quantum data processing system, such as quantum processing system 140, may contain data and may have software applications or software tools executing quantum computing processes thereon.

Clients 110, 112, and 114 are also coupled to network 102. A conventional data processing system, such as server 106, or client 110, 112, or 114 may contain data and may have software applications or software tools executing conventional computing processes thereon.

Only as an example, and without implying any limitation to such architecture, FIG. 1 depicts certain components that are usable in an example implementation of an embodiment. For example, server 106, and clients 110, 112, 114, are depicted as servers and clients only as example and not to imply a limitation to a client-server architecture. As another example, an embodiment can be distributed across several conventional data processing systems, quantum data processing systems, and a data network as shown, whereas another embodiment can be implemented on a single conventional data processing system or single quantum data processing system within the scope of the illustrative embodiments. Conventional data processing systems 106, 110, 112, and 114 also represent example nodes in a cluster, partitions, and other configurations suitable for implementing an embodiment.

Device 132 is an example of a conventional computing device described herein. For example, device 132 can take the form of a smartphone, a tablet computer, a laptop computer, client 110 in a stationary or a portable form, a wearable computing device, or any other suitable device. Any software application described as executing in another conventional data processing system in FIG. 1 can be configured to execute in device 132 in a similar manner. Any data or information stored or produced in another conventional data processing system in FIG. 1 can be configured to be stored or produced in device 132 in a similar manner.

Server 106, storage unit 108, classical processing system 104, quantum processing system 140, and clients 110, 112, and 114, and device 132 may couple to network 102 using wired connections, wireless communication protocols, or other suitable data connectivity. Clients 110, 112, and 114 may be, for example, personal computers or network computers.

In the depicted example, server 106 may provide data, such as boot files, operating system images, and applications to clients 110, 112, and 114. Clients 110, 112, and 114 may be clients to server 106 in this example. Clients 110, 112, 114, or some combination thereof, may include their own data, boot files, operating system images, and applications. Data processing environment 100 may include additional servers, clients, and other devices that are not shown.

In the depicted example, memory 124 may provide data, such as boot files, operating system images, and applications to classical processor 122. Classical processor 122 may include its own data, boot files, operating system images, and applications. Data processing environment 100 may include additional memories, quantum processors, and other devices that are not shown. Memory 124 includes application 105 that may be configured to implement one or more of the classical processor functions described herein for calculating excited state energies of a molecular system on a hybrid classical-quantum computing system in accordance with one or more embodiments.

In the depicted example, memory 144 may provide data, such as boot files, operating system images, and applications to quantum processor 142. Quantum processor 142 may include its own data, boot files, operating system images, and applications. Data processing environment 100 may include additional memories, quantum processors, and other devices that are not shown. Memory 144 includes application 146 that may be configured to implement one or more of the quantum processor functions described herein in accordance with one or more embodiments.

In the depicted example, data processing environment 100 may be the Internet. Network 102 may represent a collection of networks and gateways that use the Transmission Control Protocol/Internet Protocol (TCP/IP) and other protocols to communicate with one another. At the heart of the Internet is a backbone of data communication links between major nodes or host computers, including thousands of commercial, governmental, educational, and other computer systems that route data and messages. Of course, data processing environment 100 also may be implemented as a number of different types of networks, such as for example, an intranet, a local area network (LAN), or a wide area network (WAN). FIG. 1 is intended as an example, and not as an architectural limitation for the different illustrative embodiments.

Among other uses, data processing environment 100 may be used for implementing a client-server environment in which the illustrative embodiments may be implemented. A client-server environment enables software applications and data to be distributed across a network such that an application functions by using the interactivity between a conventional client data processing system and a conventional server data processing system. Data processing environment 100 may also employ a service oriented architecture where interoperable software components distributed across a network may be packaged together as coherent business applications. Data processing environment 100 may also take the form of a cloud, and employ a cloud computing model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service.

With reference to FIG. 2, this figure depicts a block diagram of a data processing system in which illustrative embodiments may be implemented. Data processing system 200 is an example of a conventional computer, such as classical processing system 104, server 106, or clients 110, 112, and 114 in FIG. 1, or another type of device in which computer usable program code or instructions implementing the processes may be located for the illustrative embodiments.

Data processing system 200 is also representative of a conventional data processing system or a configuration therein, such as conventional data processing system 132 in FIG. 1 in which computer usable program code or instructions implementing the processes of the illustrative embodiments may be located. Data processing system 200 is described as a computer only as an example, without being limited thereto. Implementations in the form of other devices, such as device 132 in FIG. 1, may modify data processing system 200, such as by adding a touch interface, and even eliminate certain depicted components from data processing system 200 without departing from the general description of the operations and functions of data processing system 200 described herein.

In the depicted example, data processing system 200 employs a hub architecture including North Bridge and memory controller hub (NB/MCH) 202 and South Bridge and input/output (I/O) controller hub (SB/ICH) 204. Processing unit 206, main memory 208, and graphics processor 210 are coupled to North Bridge and memory controller hub (NB/MCH) 202. Processing unit 206 may contain one or more processors and may be implemented using one or more heterogeneous processor systems. Processing unit 206 may be a multi-core processor. Graphics processor 210 may be coupled to NB/MCH 202 through an accelerated graphics port (AGP) in certain implementations.

In the depicted example, local area network (LAN) adapter 212 is coupled to South Bridge and I/O controller hub (SB/ICH) 204. Audio adapter 216, keyboard and mouse adapter 220, modem 222, read only memory (ROM) 224, universal serial bus (USB) and other ports 232, and PCI/PCIe devices 234 are coupled to South Bridge and I/O controller hub 204 through bus 238. Hard disk drive (HDD) or solid-state drive (SSD) 226 and CD-ROM 230 are coupled to South Bridge and I/O controller hub 204 through bus 240. PCI/PCIe devices 234 may include, for example, Ethernet adapters, add-in cards, and PC cards for notebook computers. PCI uses a card bus controller, while PCIe does not. ROM 224 may be, for example, a flash binary input/output system (BIOS). Hard disk drive 226 and CD-ROM 230 may use, for example, an integrated drive electronics (IDE), serial advanced technology attachment (SATA) interface, or variants such as external-SATA (eSATA) and micro-SATA (mSATA). A super I/O (SIO) device 236 may be coupled to South Bridge and I/O controller hub (SB/ICH) 204 through bus 238.

Memories, such as main memory 208, ROM 224, or flash memory (not shown), are some examples of computer usable storage devices. Hard disk drive or solid state drive 226, CD-ROM 230, and other similarly usable devices are some examples of computer usable storage devices including a computer usable storage medium.

An operating system runs on processing unit 206. The operating system coordinates and provides control of various components within data processing system 200 in FIG. 2. The operating system may be a commercially available operating system for any type of computing platform, including but not limited to server systems, personal computers, and mobile devices. An object oriented or other type of programming system may operate in conjunction with the operating system and provide calls to the operating system from programs or applications executing on data processing system 200.

Instructions for the operating system, the object-oriented programming system, and applications or programs, such as application 105 in FIG. 1, are located on storage devices, such as in the form of code 226A on hard disk drive 226, and may be loaded into at least one of one or more memories, such as main memory 208, for execution by processing unit 206. The processes of the illustrative embodiments may be performed by processing unit 206 using computer implemented instructions, which may be located in a memory, such as, for example, main memory 208, read only memory 224, or in one or more peripheral devices.

Furthermore, in one case, code 226A may be downloaded over network 201A from remote system 201B, where similar code 201C is stored on a storage device 201D. In another case, code 226A may be downloaded over network 201A to remote system 201B, where downloaded code 201C is stored on a storage device 201D.

The hardware in FIGS. 1-2 may vary depending on the implementation. Other internal hardware or peripheral devices, such as flash memory, equivalent non-volatile memory, or optical disk drives and the like, may be used in addition to or in place of the hardware depicted in FIGS. 1-2. In addition, the processes of the illustrative embodiments may be applied to a multiprocessor data processing system.

In some illustrative examples, data processing system 200 may be a personal digital assistant (PDA), which is generally configured with flash memory to provide non-volatile memory for storing operating system files and/or user-generated data. A bus system may comprise one or more buses, such as a system bus, an I/O bus, and a PCI bus. Of course, the bus system may be implemented using any type of communications fabric or architecture that provides for a transfer of data between different components or devices attached to the fabric or architecture.

A communications unit may include one or more devices used to transmit and receive data, such as a modem or a network adapter. A memory may be, for example, main memory 208 or a cache, such as the cache found in North Bridge and memory controller hub 202. A processing unit may include one or more processors or CPUs.

The depicted examples in FIGS. 1-2 and above-described examples are not meant to imply architectural limitations. For example, data processing system 200 also may be a tablet computer, laptop computer, or telephone device in addition to taking the form of a mobile or wearable device.

Where a computer or data processing system is described as a virtual machine, a virtual device, or a virtual component, the virtual machine, virtual device, or the virtual component operates in the manner of data processing system 200 using virtualized manifestation of some or all components depicted in data processing system 200. For example, in a virtual machine, virtual device, or virtual component, processing unit 206 is manifested as a virtualized instance of all or some number of hardware processing units 206 available in a host data processing system, main memory 208 is manifested as a virtualized instance of all or some portion of main memory 208 that may be available in the host data processing system, and disk 226 is manifested as a virtualized instance of all or some portion of disk 226 that may be available in the host data processing system. The host data processing system in such cases is represented by data processing system 200.

Figure 3:
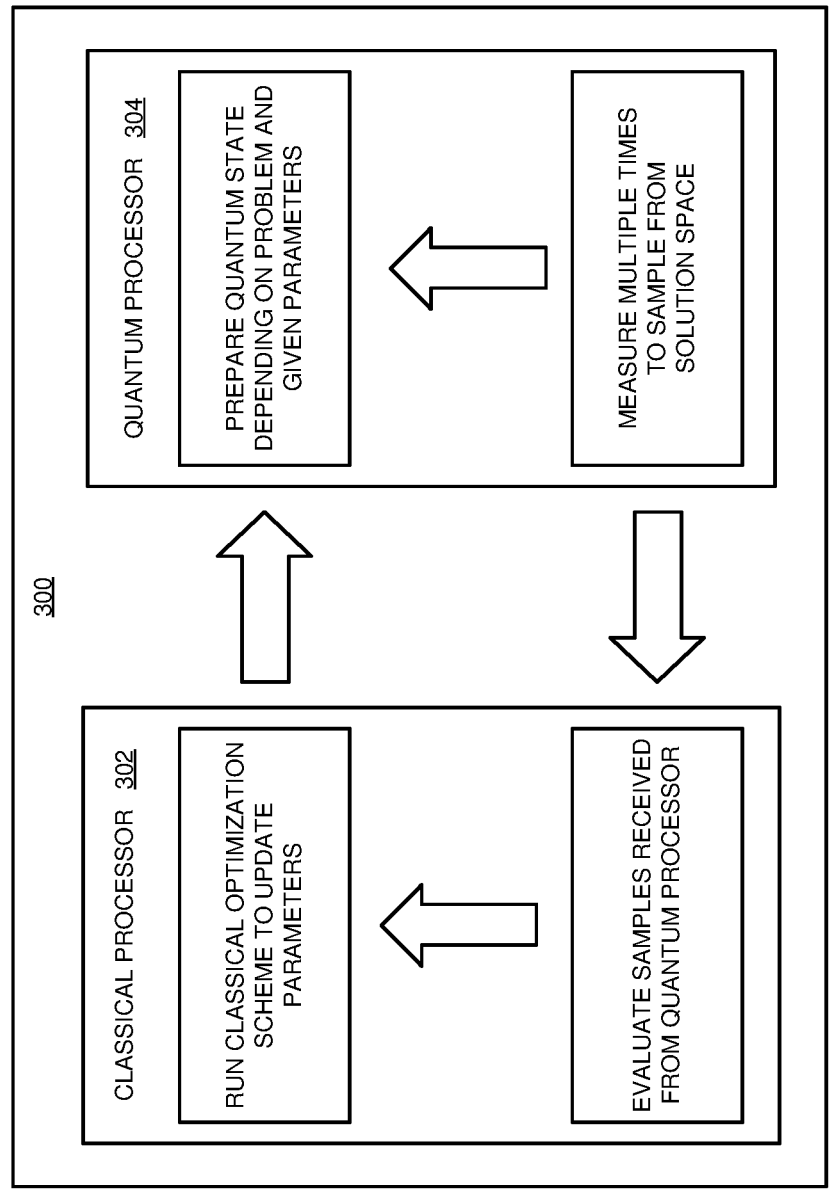
FIG. 3 depicts a block diagram of an example hybrid quantum/classical optimization algorithm for solving combinatorial optimization problems using a classical processor and a quantum processor in accordance with an illustrative embodiment.

With reference to FIG. 3, this figure depicts a block diagram of an example hybrid quantum/classical optimization algorithm 300 for solving combinatorial optimization problems using a classical processor 302 and a quantum processor 304. In the example, classical processor 302 runs a classical optimization scheme to generate update parameters for an combinatorial optimization problem and sends the update parameters to quantum processor 304. Quantum processor 304 prepares a quantum state for depending on the particular combinatorial problem to be solved and the given update parameters. Quantum processor 304 executes the prepared quantum state and measures the quantum state a multiple number of times to sample from the solution space to generate samples. Classical processor 302 receives the samples from quantum processor 304 and evaluates the received samples to determine if the parameters for the classical optimization scheme are to be updated.

If classical processor 302 determines that the parameters for the combinatorial optimization problem are to be updated, classical processor 302 runs the classical optimization scheme using the updated parameters to generated further updated parameters. Classical processor 302 then sends the further updated parameters to quantum processor 304. Typically, the process is repeated until convergence within an acceptable threshold is obtained.

Figure 4:
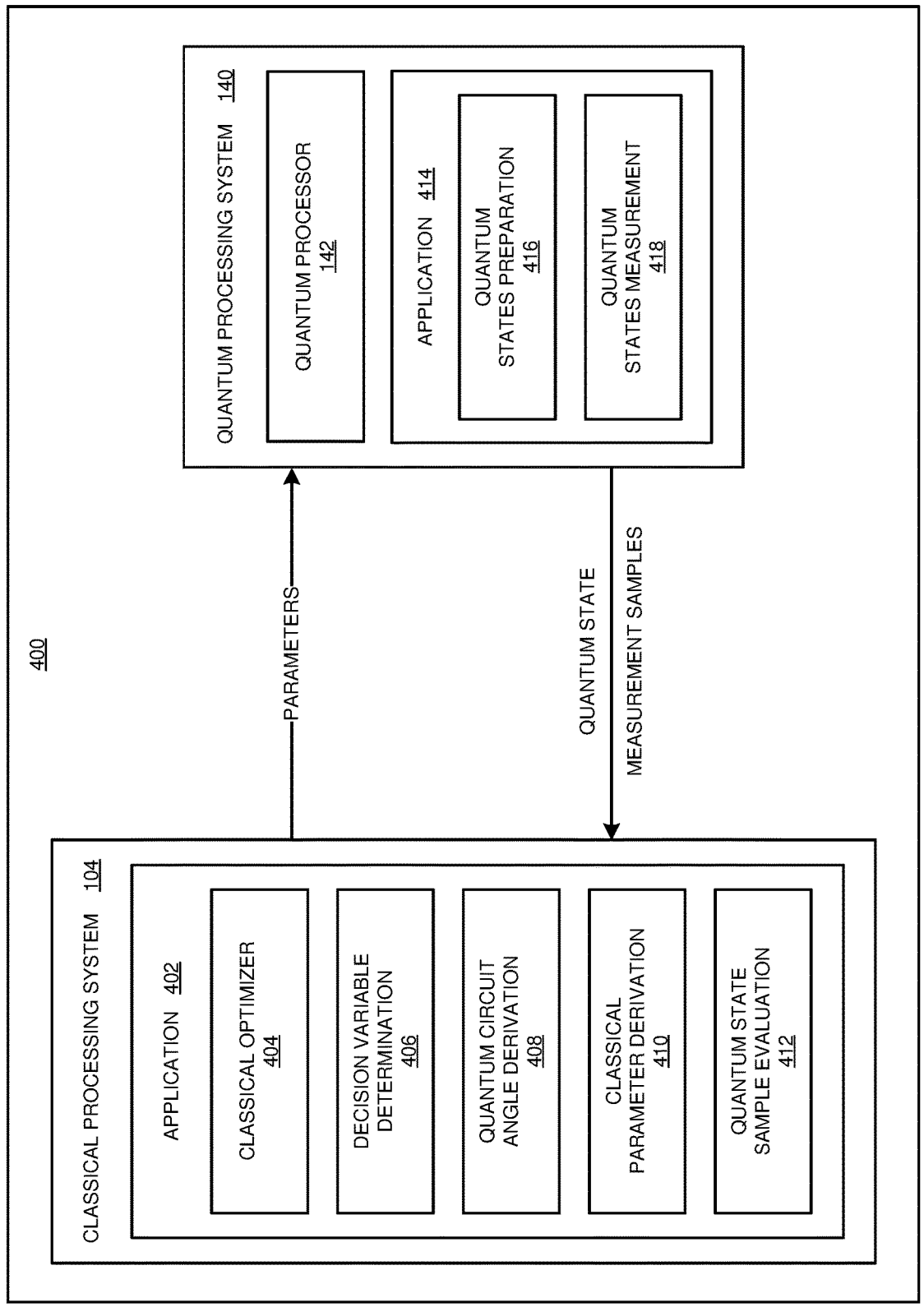
FIG. 4 depicts a block diagram of an example configuration for solving mixed integer optimization problems on a hybrid classical-quantum computing system in accordance with an illustrative embodiment.

With reference to FIG. 4, this figure depicts a block diagram of an example configuration 400 for solving mixed integer optimization problems on a hybrid classical-quantum computing system in accordance with an illustrative embodiment. The example embodiment includes classical processing system 104 and quantum processing system 140. Classical processing system 104 includes an application 402. In a particular embodiment, application 402 is an example of application 105 of FIG. 1. Application 402 includes a classical optimizer component 404, a decision variable determination component 406, a quantum circuit angle derivation component 408, a classical parameter derivation component 410, and a quantum state sample evaluation component 412.

Quantum processing system 140 includes a quantum processor 142 and an application 414. In a particular embodiment, application 414 is an example of application 146 of FIG. 1. Application 414 includes a quantum states preparation component 416 and a quantum states measurement component 418.

In the embodiment, classical optimizer component 404 is configured to execute a classical optimization scheme and utilize optimization parameter determination component 406 to generate decision variables of a classical objective function associated with a combinatorial optimization problem. In a particular embodiment, the decision variables include at least one discrete decision variable (e.g., a binary decision variable) and at least one continuous decision variable. Quantum circuit angle derivation component 408 is configured to derive quantum angles for a quantum circuit within quantum processor 142 of quantum processing system 140 from one or more of the decision variables. In a particular embodiment, quantum circuit angle derivation component 408 derives the quantum angles for the quantum circuit based upon the at least one discrete decision variable.

Classical parameter derivation component 410 is configured to derive classical parameters from one or more of the determined decision variables. In a particular embodiment, classical parameter derivation component 410 is configured to derive the classical parameters based upon the at least one continuous decision variable. Application 402 is further configured to provide the angle parameters to quantum processing system 140.

Quantum states preparation component 416 is configured to prepare one or more quantum states for the quantum circuit of quantum processor 142 based upon the quantum angles as a solution space of the problem. Quantum processor 142 then executes using the prepared quantum states as initial states of a qubit. Quantum states measurement component 418 is configured to measure intermediate quantum states a multiple of times to generate samples representative of the intermediate quantum states. In one or more embodiments, a fixed set of quantum state parameters are used to prepare the same quantum state, but measurements of the quantum state leads to probabilistic results resulting from the plurality of samples. In particular embodiments, the samples include discrete values (e.g., −1 or +1). Application 414 is further configured to send the quantum state measurement samples to application 402 of classical processing system 104.

In the embodiment, quantum state sample evaluation component 412 evaluates the quantum state measurement samples using a classical aggregation function to determine an aggregate quantum state measurement value from the samples. An aggregation function determines multiple values from a single value. In a particular embodiment, the classical aggregation function averages the quantum state measurement samples to determine a single aggregate value. In one or more embodiments, the quantum state sample evaluation component 412 evaluates the plurality of samples to obtain a measure of the quality of the quantum state and of the solutions to the mixed-integer optimization problem that can be sampled from such a quantum state. In the embodiment, quantum state sample evaluation function returns the aggregate value to classical optimizer 404. In an embodiment, application 402 determines updated decision variables based upon the aggregate value, generates updated quantum state parameters from the updated decision variables, provides the new quantum state parameters to quantum processing system 140 and the process continues iteratively until a solution is reached within a predetermine acceptable level such as after convergence.

Figure 5:
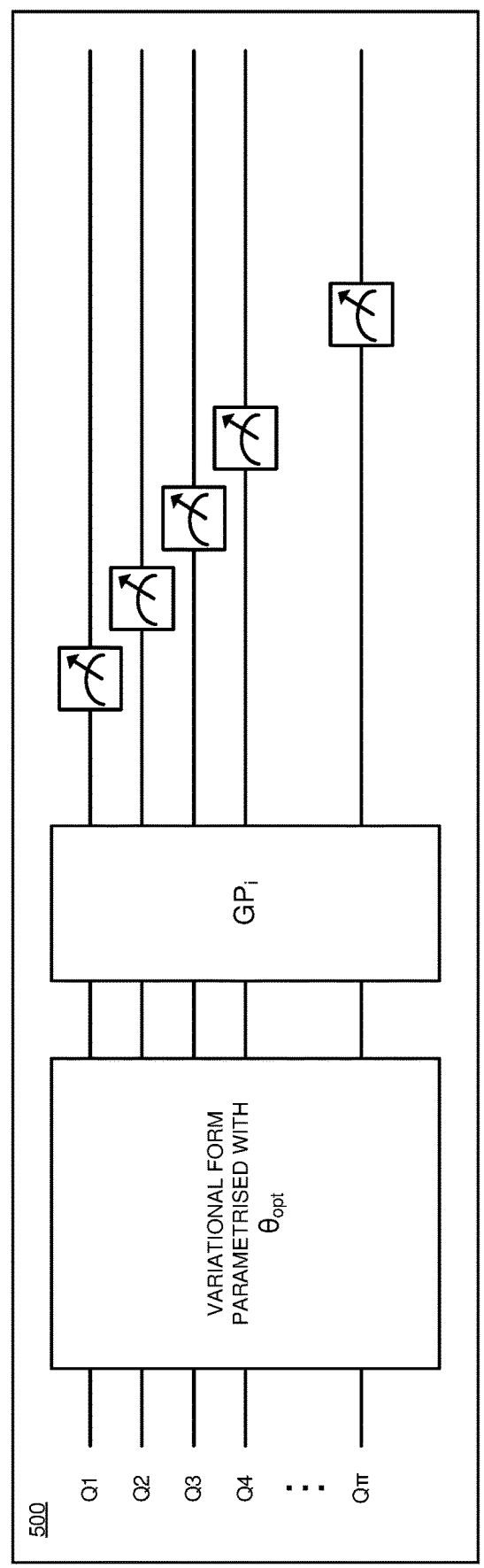
FIG. 5 depicts a block diagram of an example general quantum circuit for calculating excited state energies using a hybrid classical-quantum computing system in accordance with an illustrative embodiment.

With reference to FIG. 5, this figure depicts a block diagram of an example general quantum circuit 500 for calculating excited state energies using a hybrid classical-quantum computing system in accordance with an illustrative embodiment. Quantum circuit 500 includes a set of n qubits corresponding to the first n excitation energies. A ground state wavefunction is determined through VQE. The ground state wavefunction is parameterized in a set of angles. A set of Pauli strings are extracted and evaluated with the circuit parameterized in the set of angles. Measurements are taken on the set of qubits and then passed to a classical processor to determine eigenvalues and the excitation energies.

In the illustrated example, Quantum circuit 500 is presented as a generalized example of a quantum circuit for implementing one or more methods for calculating excited state energies as described herein. In a specific implementation, a quantum circuit may include any number of arrangements of quantum gates to implement a corresponding method for calculating excited state energies of a molecular system in accordance with one or more embodiments.

Figure 6:
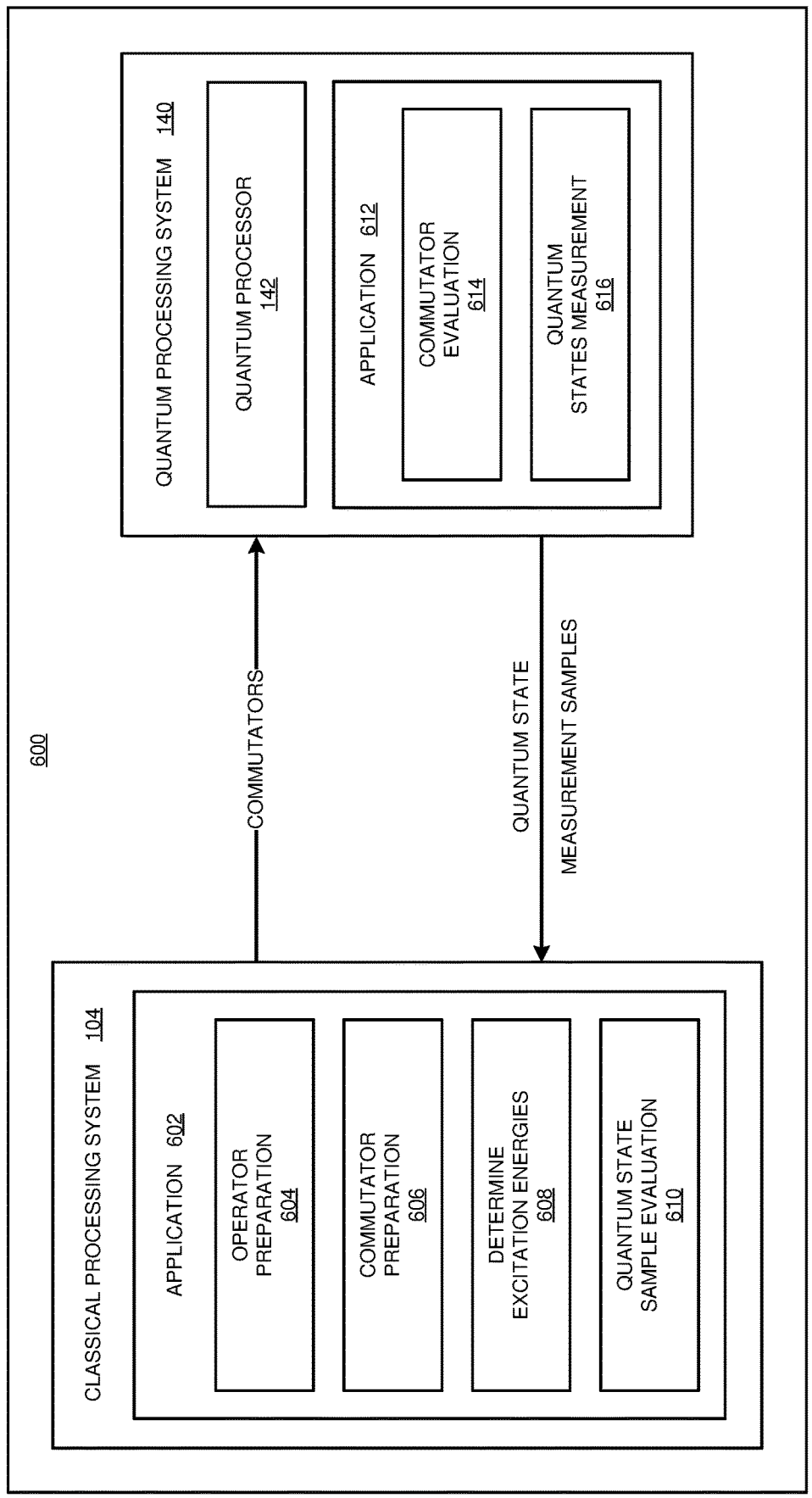
FIG. 6 depicts a block diagram of an example configuration for calculating excited state energies of a molecular system on a hybrid classical-quantum computing system in accordance with an illustrative embodiment.

With reference to FIG. 6, this figure depicts a block diagram of an example configuration 600 for calculating excited state energies of a molecular system on a hybrid classical-quantum computing system in accordance with an illustrative embodiment. The example embodiment includes classical processing system 104 and quantum processing system 140. Classical processing system 104 includes an application 602. In a particular embodiment, application 602 is an example of application 105 of FIG. 1. Application 602 includes an operator preparation component 604, a commutator preparation component 606, an excitation energy determination component 608, and a quantum state sample evaluation component 610.

Quantum processing system 140 includes a quantum processor 142 and an application 612. In a particular embodiment, application 612 is an example of application 146 of FIG. 1. Application 612 includes a commutator component 614 and a quantum states measurement component 616.

In the embodiment, operator preparation component 604 prepares excitation and de-excitation operators to determine excited states from the previously determined ground state wavefunction. In an embodiment, commutator preparation component 606 prepares commutators from the excitation operators and the Hamiltonian operator. In a particular embodiment, component 606 maps excitation operators onto a set of qubit states using Jordan-Wigner transformation. Application 602 sends the prepared commutators to application 612 of quantum processing system 140.

Commutator evaluation component 614 evaluates the set of commutators for the quantum circuit of quantum processor 142 based upon the quantum angles as a solution space of the problem. Quantum states measurement component 616 measure intermediate quantum states a multiple of times to generate samples representative of the intermediate quantum states. Application 612 is further configured to send the quantum state measurement samples to application 602 of classical processing system 104.

In the embodiment, quantum state sample evaluation component 610 evaluates the quantum state measurement samples using a classical aggregation function to determine an aggregate quantum state measurement value from the samples. An aggregation function determines multiple values from a single value. In a particular embodiment, the classical aggregation function averages the quantum state measurement samples to determine a single aggregate value. In one or more embodiments, the quantum state sample evaluation component 610 evaluates the plurality of samples to obtain the solutions to the matrix elements. In the embodiment, excitation energy determination component 608 determines a set of excitation energies using the solutions to the matrix elements.

Figure 7:
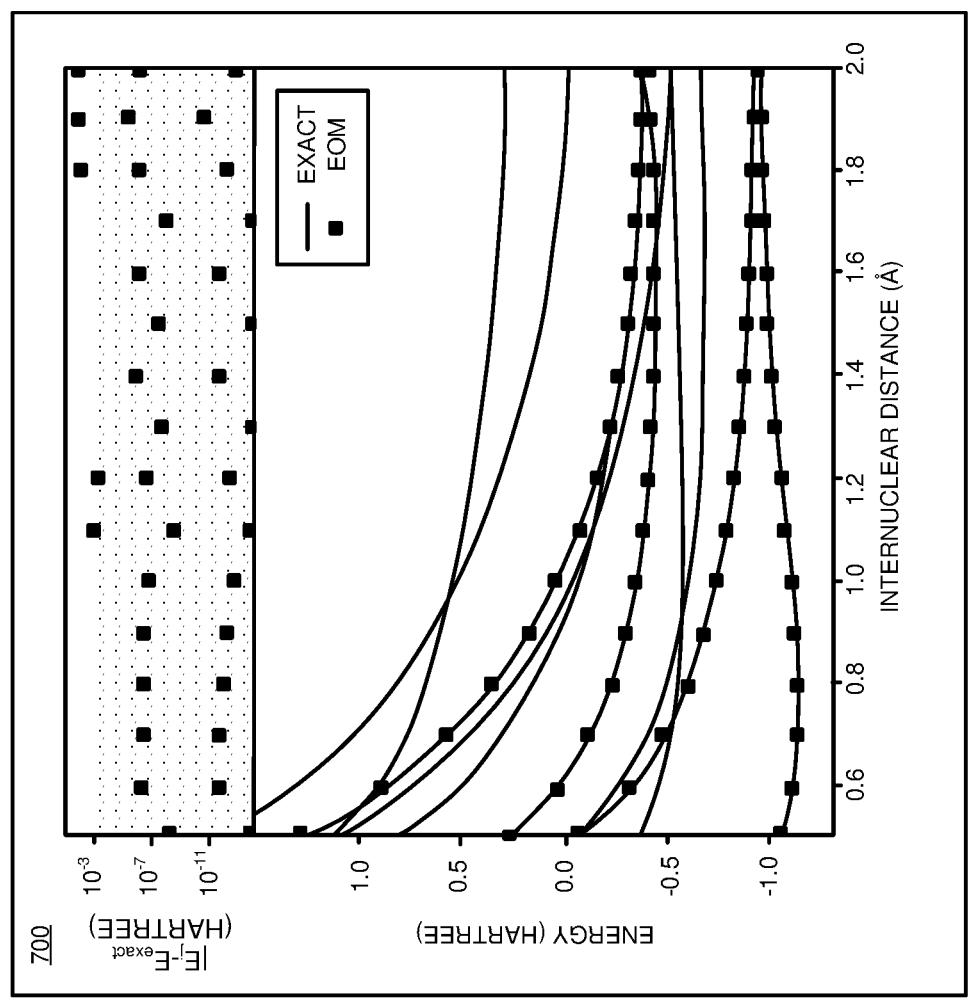
FIG. 7 depicts a graph of excitation energies calculated on a hybrid classical-quantum computing system in the manner of an illustrative embodiment.

With reference to FIG. 7, this figure depicts a graph of excitation energies calculated on a hybrid classical-quantum computing system in the manner of an illustrative embodiment. As can be seen, the difference (deviation) between the calculated excitation energies at given internuclear distance spacing and the theoretical excitation energies expected in the baseline graph is insignificant.

Figure 8:
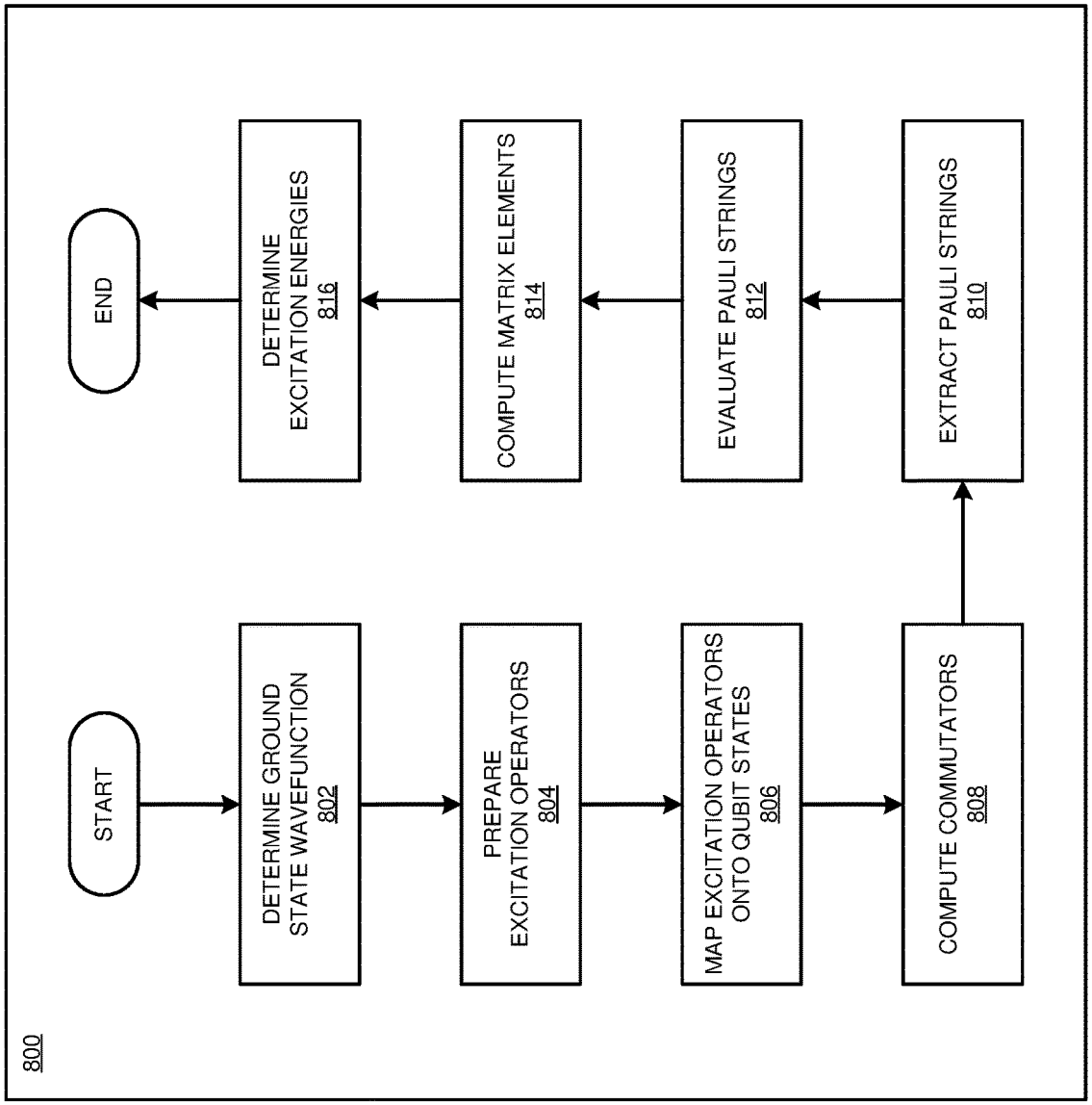
FIG. 8 depicts a flowchart of an example method for calculating excitation state energies of a molecular system on a hybrid classical-quantum computing system in accordance with an illustrative embodiment.

With reference to FIG. 8, this figure depicts a flowchart of an example method for calculating excitation state energies of a molecular system on a hybrid classical-quantum computing system in accordance with an illustrative embodiment. In block 802, quantum processor 142 determines a ground state wavefunction of a quantum system. In a particular embodiments, the ground state wavefunction is parameterized in a set of angles.

In block 804, classical processor 122 prepares a set of excitation operators for determining an excited state of the quantum system. In block 806, classical processor 122 maps the excitation operators onto a set of qubit states. In particular embodiments, the excitation operators are mapped onto a set of qubit states using the Jordan-Wigner transformation.

In block 808, classical processor 122 computes a set of commutators from the set of mapped excitation operators and a mapped Hamiltonian operator. In particular embodiments, the commutators form a set of Pauli strings, each Pauli string including a set of Pauli operators. In particular embodiments, the Hamiltonian operator is mapped onto a set of qubit states using the Jordan-Wigner transformation.

In block 810, quantum processor 142 extracts the set of Pauli strings. Quantum processor 142 groups a subset of the set of Pauli strings. In particular embodiments, the subset of the set of Pauli strings corresponds to at least one of the set of commutators. In block 812, quantum processor 142 evaluates the set of Pauli strings with a quantum circuit parameterized in the set of angles corresponding to the ground state wavefunction.

In block 814, classical processor 122 computes a set of matrix elements from the set of commutators. In block 816, classical processor 122 determines a set of excitation energies from the set of matrix elements. In particular embodiments, classical processor 122 computes a set of eigenvalues to determine the set of excitation energies.

Thus, a computer implemented method, system or apparatus, and computer program product are provided in the illustrative embodiments for calculating excitation state energies of a molecular system using a hybrid classical-quantum computing system and other related features, functions, or operations. Where an embodiment or a portion thereof is described with respect to a type of device, the computer implemented method, system or apparatus, the computer program product, or a portion thereof, are adapted or configured for use with a suitable and comparable manifestation of that type of device.

Where an embodiment is described as implemented in an application, the delivery of the application in a Software as a Service (SaaS) model is contemplated within the scope of the illustrative embodiments. In a SaaS model, the capability of the application implementing an embodiment is provided to a user by executing the application in a cloud infrastructure. The user can access the application using a variety of client devices through a thin client interface such as a web browser (e.g., web-based e-mail), or other light-weight client-applications. The user does not manage or control the underlying cloud infrastructure including the network, servers, operating systems, or the storage of the cloud infrastructure. In some cases, the user may not even manage or control the capabilities of the SaaS application. In some other cases, the SaaS implementation of the application may permit a possible exception of limited user-specific application configuration settings.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, including but not limited to computer-readable storage devices as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method comprising:
   determining, using a quantum processor and memory, a ground state wavefunction of a combination of quantum logic gates, the quantum processor comprising a set of quantum logic gates configured to perform single qubit rotations;
   forming a set of excitation operators, the set of excitation operators configured to determine an excited state wavefunction from the ground state wavefunction;
   forming a set of commutators of the set of excitation operators and a Hamiltonian operator, the Hamiltonian operator configured to determine a ground state energy of a wavefunction;
   mapping the set of commutators onto a set of qubit states, the set of qubit states corresponding to a set of qubits of the quantum processor;
   evaluating, using the quantum processor and memory, the set of commutators; and
   causing a quantum readout circuit to measure an excited state energy from the set of computed commutators.

2. The method of claim 1, further comprising:
   extracting a set of Pauli strings, each Pauli string of the set of Pauli strings comprising a set of Pauli operators.

3. The method of claim 2, further comprising:
   evaluating the set of Pauli strings to compute the set of commutators.

4. The method of claim 2, further comprising:
   grouping a subset of the set of Pauli strings, the subset corresponding to at least one of the set of commutators.

5. The method of claim 1, further comprising:
   mapping the set of excitation operators using Jordan-Wigner transformation.

6. The method of claim 1, wherein the set of commutators are mapped using Jordan-Wigner transformation.

7. The method of claim 1, further comprising:
   computing, from the set of commutators, a set of matrix elements for a secular matrix equation; and
   computing, using the set of matrix elements, a set of eigenvalues corresponding to a set of excitation energies.

8. The method of claim 1, wherein the set of commutators is formed using a classical processor, and wherein the set of commutators is mapped, using Jordan-Wigner transformation and the classical processor, onto the set of qubit states prior to sending the mapped set of commutators from the classical processor to the quantum processor.

9. A computer usable program product comprising one or more computer-readable storage devices, and program instructions stored on at least one of the one or more storage devices, the stored program instructions comprising:

program instructions to determine, using a quantum processor and memory, a ground state wavefunction of a combination of quantum logic gates, the quantum processor comprising a set of quantum logic gates configured to perform single qubit rotations;

program instructions to form a set of excitation operators, the set of excitation operators configured to determine an excited state wavefunction from the ground state wavefunction;

program instructions to form a set of commutators of the set of excitation operators and a Hamiltonian operator, the Hamiltonian operator configured to determine a ground state energy of a wavefunction;

program instructions to map the set of commutators onto a set of qubit states, the set of qubit states corresponding to a set of qubits of the quantum processor;

program instructions to evaluate, using the quantum processor and memory, the set of commutators; and program instructions to cause a quantum readout circuit to measure an excited state energy from the set of computed commutators.

10. The computer usable program product of claim 9, wherein the program instructions are stored in a computer readable storage device in a data processing system, and wherein the program instructions are transferred over a network from a remote data processing system.

11. The computer usable program product of claim 9, wherein the program instructions are stored in a computer readable storage device in a server data processing system, and wherein the program instructions are downloaded over a network to a remote data processing system for use in a computer readable storage device associated with the remote data processing system.

12. The computer usable program product of claim 9, further comprising:

program instructions to extract a set of Pauli strings, each Pauli string of the set of Pauli strings comprising a set of Pauli operators.

13. The computer usable program product of claim 12, further comprising:

program instructions to evaluate the set of Pauli strings to compute the set of commutators.

14. The computer usable program product of claim 12, further comprising:

program instructions to group a subset of the set of Pauli strings, the subset corresponding to at least one of the set of commutators.

15. The computer usable program product of claim 9, further comprising:

program instructions to map the set of excitation operators using Jordan-Wigner transformation.

16. The computer usable program product of claim 9, further comprising:

program instructions to compute, from the set of commutators, a set of matrix elements for a secular matrix equation; and program instructions to compute, using the set of matrix elements, a set of eigenvalues corresponding to a set of excitation energies.

17. A computer system comprising one or more processors, one or more computer-readable memories, and one or more computer-readable storage devices, and program instructions stored on at least one of the one or more storage devices for execution by at least one of the one or more processors via at least one of the one or more memories, the stored program instructions comprising:

program instructions to determine, using a quantum processor and memory, a ground state wavefunction of a combination of quantum logic gates, the quantum processor comprising a set of quantum logic gates configured to perform single qubit rotations;

program instructions to form a set of excitation operators, the set of excitation operators configured to determine an excited state wavefunction from the ground state wavefunction;

program instructions to form a set of commutators of the set of excitation operators and a Hamiltonian operator, the Hamiltonian operator configured to determine a ground state energy of a wavefunction;

program instructions to map the set of commutators onto a set of qubit states, the set of qubit states corresponding to a set of qubits of the quantum processor;

program instructions to evaluate, using the quantum processor and memory, the set of commutators; and program instructions to cause a quantum readout circuit to measure an excited state energy from the set of computed commutators.

18. The computer system of claim 17, further comprising:

program instructions to extract a set of Pauli strings, each Pauli string of the set of Pauli strings comprising a set of Pauli operators.

19. The computer system of claim 18, further comprising:

program instructions to evaluate the set of Pauli strings to compute the set of commutators.

20. The computer system of claim 18, further comprising:

program instructions to group a subset of the set of Pauli strings, the subset corresponding to at least one of the set of commutators.

* * * * *